(12) United States Patent
Halsmer

(10) Patent No.: US 6,748,806 B2
(45) Date of Patent: Jun. 15, 2004

(54) DYNAMIC BALANCING SYSTEM FOR COMPUTED TOMOGRAPHY GANTRY

(75) Inventor: Matthew A. Halsmer, Waukesha, WI (US)

(73) Assignee: GE Medical Systems Global Technology Company LLC, Waukesha, WI (US)

( * ) Notice: Subject to any disclaimer, the term of this patent is extended or adjusted under 35 U.S.C. 154(b) by 0 days.

(21) Appl. No.: 10/084,696

(22) Filed: Feb. 27, 2002

(65) Prior Publication Data

US 2003/0159508 A1 Aug. 28, 2003

(51) Int. Cl.[7] ............................. G01M 1/16; H05G 1/28
(52) U.S. Cl. ........................ 73/462; 73/468; 378/162
(58) Field of Search ...................... 73/462, 460, 468, 73/65.01, 483; 378/207, 4, 162

(56) References Cited

FOREIGN PATENT DOCUMENTS

JP          2001/70038 A    *  6/2001     ............ A61B/6/03

* cited by examiner

Primary Examiner—Helen Kwok
(74) Attorney, Agent, or Firm—Quarles & Brady LLP; Carl Horton

(57) ABSTRACT

Static and/or dynamic balancing of a CT gantry is provided by electronically positionable masses incorporated into the gantry structure that may be moved to nullify gantry imbalances caused by variation in components specifications or replacement of components on a balanced gantry.

5 Claims, 2 Drawing Sheets

DYNAMIC BALANCING SYSTEM FOR COMPUTED TOMOGRAPHY GANTRY

CROSS-REFERENCE TO RELATED APPLICATIONS

Not applicable

STATEMENT REGARDING FEDERALLY SPONSORED RESEARCH OR DEVELOPMENT

Not applicable

BACKGROUND OF THE INVENTION

Current computed tomography (CT) imaging systems may provide an annular gantry that receives a patient within a gantry bore and rotates about the patient.

The gantry supports an x-ray source to project, for example, a fan shaped x-ray beam extending along the plane of rotation of the gantry toward the bore. The x-ray beam will thus pass through the patient where it is then received by a detector array. The detector array is held on the gantry opposite to the x-ray source with respect to the bore.

As the gantry rotates, a series of x-ray projections of a "slice" of the patient are obtained at different angles. These projections are reconstructed mathematically, for example, using the well known filtered back projection algorithm, to create a tomographic image of that slice. The patient may be moved axially through the bore to obtain data on adjacent slices which may be assembled to provide data about arbitrary volumes of interest within the patient.

The rotational speed of the gantry affects the time necessary to obtain the tomographic image and thus, generally, higher speeds of rotation of the gantry are desired. Higher speeds increase the importance of static and dynamic balance of the gantry.

Current approaches to balancing the gantry attempt to control the center of gravity and mass of the components mounted on the gantry, to a tight specification, so that the assembled system is within balance. These components generally include the x-ray source and detector, signal processing circuitry, power supplies and cooling systems. The gantry may then be manually balanced by the addition of weights or movement of components, a time consuming and difficult task.

The need to precisely control of the center of gravity and mass of the components on the gantry increases the cost of these components. Tight specification of center of gravity and mass hamper design improvements and make multiple sourcing of the components more difficult. When a component is replaced in the field, the gantry may need to be rebalanced. Such field rebalancing is more difficult than balancing during manufacturing when the greater accessibility to the gantry, balancing weights, and balancing tools may be had.

BRIEF SUMMARY OF THE INVENTION

The present invention attaches at least one electronically positionable weight to the gantry during the manufacturing process or in a retrofit operation. Movement of the weight corrects for imbalance and thereby allows much reduced tolerances for the mass and center of gravity of the gantry components. The weight may be optimally positioned on the gantry without concern for accessibility because it is electronically controlled. The electronic control further allows for the implementation of automatic balancing mechanisms that may be easily performed in the factory or in the field.

A key to the invention is the recognition that a limited set of such electronically positionable weights may provide for arbitrary static and dynamic gantry balancing, however, subsets of this ideal set of weights may also be used to advantage.

DETAILED DESCRIPTION OF THE PREFERRED EMBODIMENT

Figure 1:
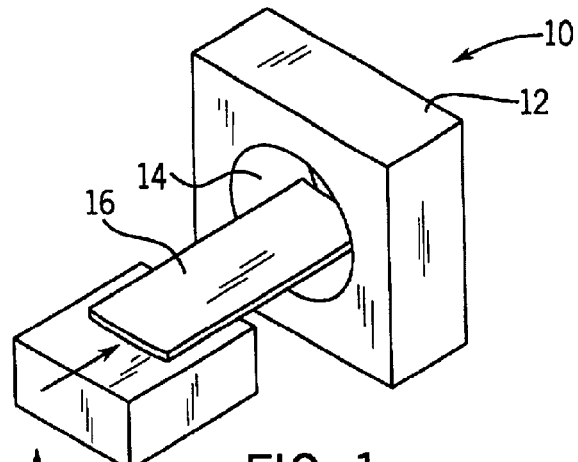
FIG. 1 is a simplified perspective view of a CT system showing a table for movement along a w-axis within the bore of a gantry housing that contains a rotating gantry.

Referring now to FIG. 1, a computed tomography machine 10 includes a gantry housing 12 having a central bore 14 directed along a w-axis. The w-axis is generally perpendicular to an imaging plane passing through the gantry housing 12 and described by Cartesian coordinates x and y. A patient table 16 may be inserted along the w-axis into the bore 14 for scanning of a patient lying on the table 16.

Figure 2:
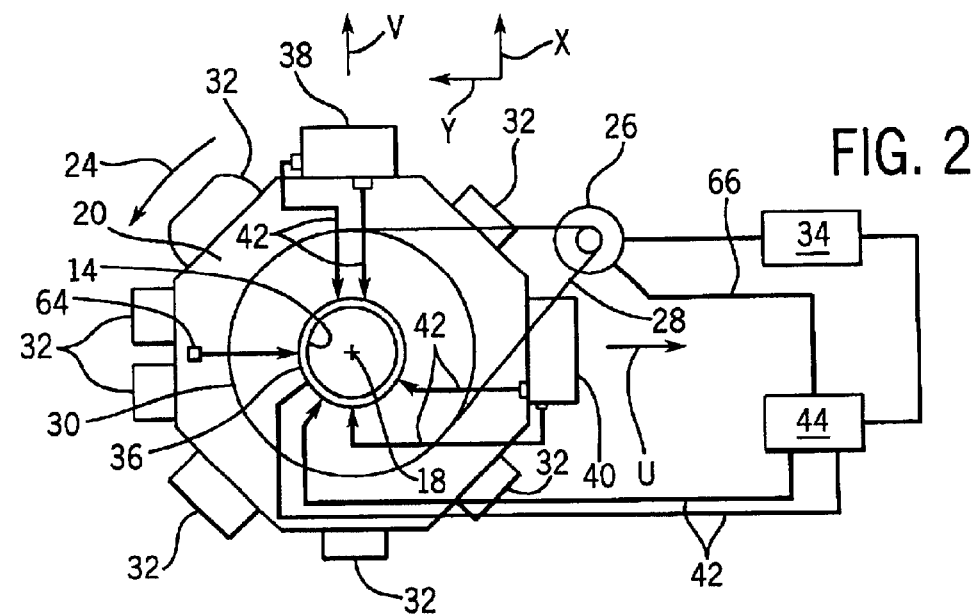
FIG. 2 is a generalized elevational view of the rotating gantry showing the position of two motorized weight units on rotating u- and v-axes, and further showing a controller with which the motorized weight units may communicate for automatic gantry balancing.

Referring to FIG. 2, an annular gantry 20 is contained within the gantry housing 12, the gantry extending generally along the image plane and supported to rotate within the image plane about the w-axis as indicated by arrow 24. A motor 26 communicating by means of a belt 28 with a gantry drive ring 30, drives the gantry 20.

The gantry 20 supports a number of components 32 including but not limited to: an x-ray tube and its collimation mechanism, an x-ray detector, a data acquisition system, power supplies and cooling systems such as are well known in the art. Generally, the location of the components 32 on the gantry 20 and their mass and centers of gravity are defined so that the gantry 20 operating at its normal rotational speed is approximately statically and dynamically balanced. Precise dynamic and static balancing will normally not be obtained at desired levels of manufacturing tolerances both in the components 32 and their placement on the gantry 20.

The various components 32 communicate with a stationary CT controller 34 through a set of slip rings 36 providing for the interchange of data and power. CT controller 34 also controls motor 26 and provides process signals and CT images to the user of a type well known in the art.

In one embodiment of the present invention, two motorized weight units 38 and 40 are attached to the gantry 20 along a v and u-axis, respectively. The v and u-axes lie in the x-y plane but are fixed relative to the gantry 20 to rotate therewith. The u- and v-axes intersect the center of rotation 18 of the gantry 20 and are perpendicular to each other. The two motorized weight units 38 and 40 are, in this embodiment, positioned at equal and maximum practical radius from the center of rotation 18. These locations and the number of two motorized weight units, while preferred, are not mandatory to the invention.

The motorized weight units 38 and 40 each receive two position signals through lines 42 communicating with a balance controller 44, for example, by the slip rings 36, optical or radio frequency links or other methods well known in the art. Alternatively, the balance controller 44 could be on the gantry itself. Balance controller 44, whose operation will be described in detail below, may be a separate control circuit or may be incorporated into the CT controller 34 either as discrete circuitry or software operating on a processor.

Figure 3:
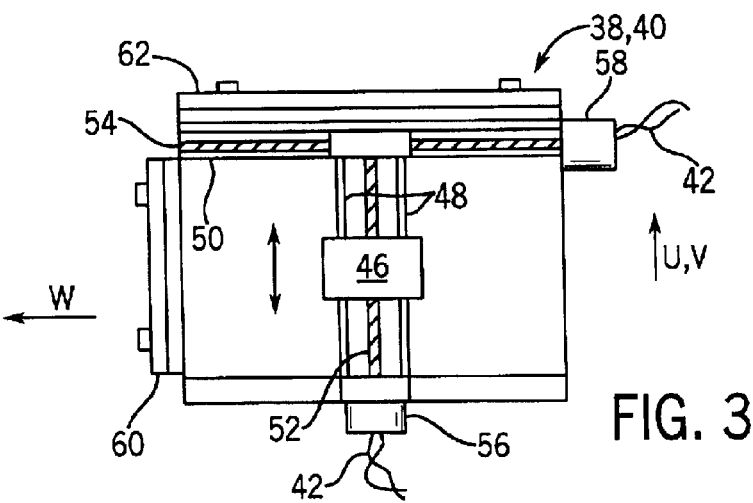
FIG. 3 is a elevational view of one motorized weight unit of FIG. 2 showing a weight moveable along the u- or v-axes and the w-axis under the control of corresponding motors, the motorized weight unit having an optional mounting point for additional weight plates.

Referring now also to FIG. 3, each of the motorized weight units 38 and 40 includes a weight 46 supported on perpendicular guide tracks 48 and 50 so as to be movable in two mutually perpendicular directions under the control of lead screws 52 and 54, the former attached to servo motor 56 and the latter attached to servo motor 58. It will be understood that other actuators may be used in place of a servo motor and lead screws including stepper motors and pneumatic and hydraulic actuators or the like.

A first axis of movement of each of the motorized weight units 38 and 40 is aligned with the w-axis and a second axis of movement of the motorized weight units 38 and 40 is aligned with either one of the u-or v-axes. Thus, radial motion in one of two perpendicular directions (u or v) may be obtained from each of the motorized weight units 38 and 40 generally allowing for the balancing out of in-plane forces of imbalance such as would tend to cause radial forces on the gantry 20. In addition, axial motion (w) may be obtained from each of the motorized weight units 38 and 40 generally allowing for the balancing of out-of-plane forces such as would tend to tip the rotation of the gantry 20.

The motorized weight units 38 and 40 are preferably mounted on the gantry 20 with the weights 46 initially centered along the guide tracks 48 and 50 and aligned with the u- or v-axis of gantry 20. Deviation in the specified mass or center of gravity of components 32 or their mounting location may then be accommodated by motion of the weights 46 in any of four directions (plus or minus u or v, and plus or minus w). The mass of the weights 46 and the range of travel of the weights 46 are tailored to the particular gantry 20 and its components 32 and the desired tolerance of mass and center of gravity and placement of the components 32 (and hence the amount of balance correction required) as may be determined according to principles understood to those of ordinary skill in the art.

Optionally, the motorized weight units 38 and 40 may include mounting points for weight plates 60 and 62 to augment the balancing process as may be required during initial manufacturing when many components must be balanced. The mounting points for the weight plates 62 are preferably at points displaced from the center of motorized weight units 38 and 40 along the u- or v-axis and the mounting points for weight plates 60 are preferably at points displaced from the center of motorized weight units 38 and 40 along the w-axis. Generally, the weight plates 60 and 62 allow for fundamental changes in the components 32 such as may occur during model changes.

The pitch of the lead screws 52 and 54 and the residual torque of the servo motors 56 and 58 may be selected so that in the absence of power to motors 56 and 58, the weight 46 remains stationary, but upon application of power in the form of a position signal, the weight 46 may be moved within the confines of the plane defined by the guide tracks 48 and 50.

Referring again to FIG. 2, a number of sensors 64 may be placed on the gantry or the gantry bearings (not shown) so as to detect forces indicative of out of balance operation of the gantry 20. These sensors 64 may be accelerometers detecting movement of the gantry 20 under the influence of out-of-plane or in-plane forces or may be strain gages detecting flexure under similar situations. In addition, a torque sensor line 66 may be received from the motor 26 indicating variations in torque necessary to rotate the gantry 20.

The movement of the weights 46 necessary for balancing of the gantry 20 may be done manually by direct control of the signals on leads 42 through a control panel or the like. Preferably, however, an automatic balancing procedure is used in which balance controller 44 measures signals from the sensor 64 and motor 26 to provide control of the weights 46 within the motorized weight units 38 and 40.

Figure 4:
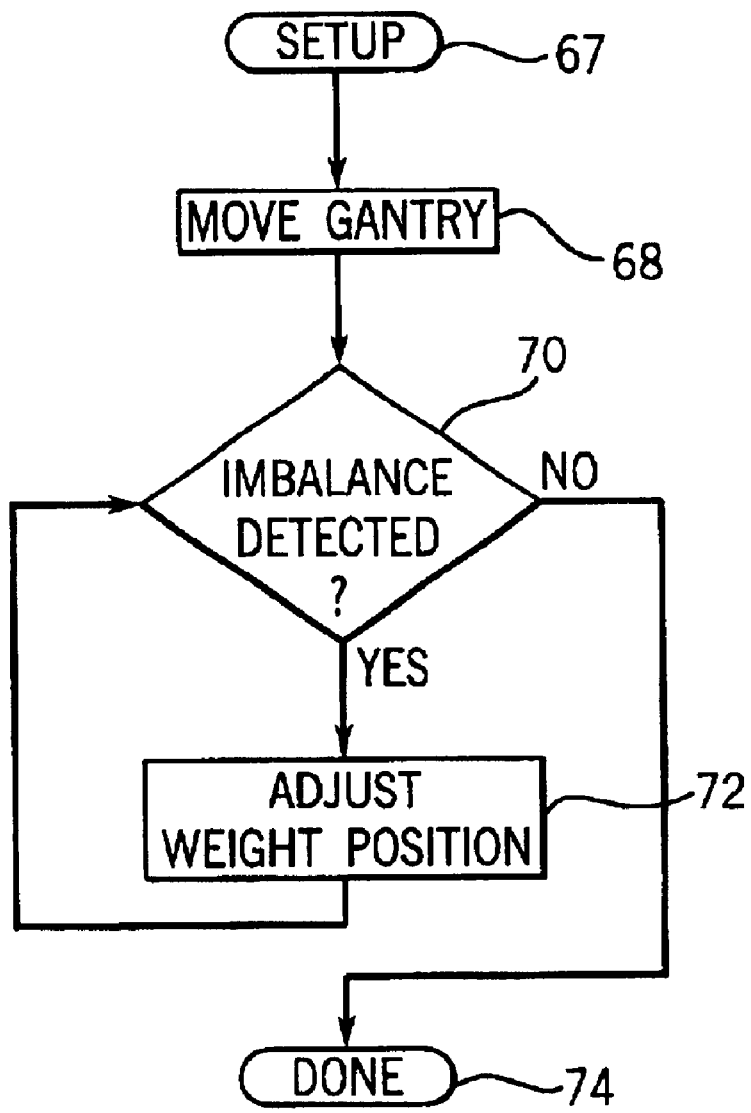
FIG. 4 is a flow chart showing the steps of operation of the controller of FIG. 2 in performing an automatic balancing of the gantry.

Referring now to FIG. 4, an automatic balance set up process executed on balance controller 44 is entered at process block 67. At succeeding process block 68, the gantry 20 is rotated so as to reveal information about imbalance. In a simple static balancing process, the gantry 20 may be rotated slowly to suppress dynamic imbalances and changes in the force of moving of the gantry 20 (read as changes in torque from motor 26) caused by static imbalance acted on by gravitational attraction, may be detected to map out a static balance error. This error is detected at decision block 70 resulting in an adjustment of the weights at block 72 until balance in corrected. This process may be iterative, for example, by deducing an imbalance vector and moving the weights to reduce this vector magnitude or may be performed by computational derivation of the displaced center of gravity of the gantry 20 and movement of the weights 46 accordingly. At process block 72 limits of travel of the weights 46 may be detected and the operator signaled that weight plates 60 or 62 must be added.

Alternatively, or in addition, the motion of the gantry 20 at block 68 may be such as to represent normal rotational speeds of the gantry 20 such as produces both static and dynamic imbalance. Again, the imbalance may be detected at decision block 70 and motion of the weights 46 provided either according to an iterative optimization process or by derivation of absolute imbalance mounts the signals of the sensors 64. This process may be simplified by a first elimination of static imbalances as described above.

When the imbalance is corrected to beneath a desired imbalance threshold, the program is done as indicated by process block 74.

Placement of the motorized weight units 38 and 40 in perpendicular relationship toward the periphery of the gantry 20 improves the corrective abilities of the weights 46, however, it will be understood that other positions are also acceptable with general balancing obtained so long as perpendicular axes of motion may be obtained along u, v and w at least in components of the movement of the weights. Further, it will be understood that limited balancing can be obtained with a weight moveable in only one of these axes. Although the inventors do not wish to be bound by a particular theory, it is believed that with the three axis motion described above, any imbalance of the gantry may be corrected both in-plane and out-of-plane, static and dynamic, provided sufficient weight and range of travel may be obtained.

It is specifically intended that the present invention not be limited to the embodiments and illustrations contained herein, but that modified forms of those embodiments including portions of the embodiments and combinations of elements of different embodiments also be included as come within the scope of the following claims.

I claim:

1. A dynamic balancing system for a computer tomography gantry, the gantry rotating about a gantry axis and supporting components for acquisition of tomographic data, the balancing system comprising:

at least one electronically positionable weight attached to the gantry for movement with respect to the gantry along the gantry axis according to a received position signal to correct imbalance in the gantry caused by variation in the components;

wherein the electronically positionable weight is movable along two weight axes having components of motion parallel to the gantry axis and radial to the gantry axis, respectively, each receiving an independent position signal.

2. A dynamic balancing system for a computer tomography gantry, the gantry rotating about a gantry axis and supporting components for acquisition of tomographic data, the balancing system comprising:

at least one electronically positionable weight attached to the gantry for movement with respect to the gantry along two axes according to two received position signals to correct imbalance in the gantry caused by variation in the components.

3. The dynamic balancing system of claim 2 including two electronically positionable weights, each attached at spatially separated points on the gantry, each receiving an independent position signal.

4. The dynamic balancing system of claim 3 wherein the two electronically positionable weights are positioned along lines of radius from the gantry axis that are perpendicular to each other.

5. The dynamic balancing system of claim 2 wherein each of the electronically positionable weights are movable along an independent weight axis, wherein the weight axes are perpendicular to each other.

* * * * *